United States Patent
Hogen et al.

(10) Patent No.: US 7,527,941 B1
(45) Date of Patent: May 5, 2009

(54) PROCESS FOR PRODUCING ETHYL ALCOHOL FROM CELLULOSIC MATERIALS

(75) Inventors: Delman R. Hogen, Spring Lake Park, MN (US); Timothy T. France, Elk River, MN (US)

(73) Assignee: Clear Water Technologies, Inc., Fridley, MN (US)

( * ) Notice: Subject to any disclaimer, the term of this patent is extended or adjusted under 35 U.S.C. 154(b) by 330 days.

(21) Appl. No.: 11/439,877

(22) Filed: May 24, 2006

(51) Int. Cl.
*C12P 39/00* (2006.01)
*C12P 19/04* (2006.01)
*C12P 19/02* (2006.01)
*C12P 7/06* (2006.01)
*C12P 7/10* (2006.01)

(52) U.S. Cl. .................. 435/42; 435/101; 435/105; 435/161; 435/165

(58) Field of Classification Search .............. None
See application file for complete search history.

(56) References Cited

U.S. PATENT DOCUMENTS

| | | | |
|---|---|---|---|
| 4,094,742 A | 6/1978 | Bellamy | 195/33 |
| 4,321,328 A | 3/1982 | Hoge | 435/191 |
| 4,393,136 A | 7/1983 | Cheetham | 435/161 |
| 4,647,534 A | 3/1987 | Lawford | 435/162 |
| 4,731,329 A | 3/1988 | Lawford | 435/162 |
| 4,830,964 A | 5/1989 | Lawford | 435/162 |
| 5,100,791 A | 3/1992 | Spindler et al. | 435/163 |
| 5,360,737 A * | 11/1994 | Ishii et al. | 435/252.1 |
| 5,648,264 A * | 7/1997 | Kume | 435/264 |
| 5,705,369 A * | 1/1998 | Torget et al. | 435/105 |
| 6,020,324 A * | 2/2000 | Jamas et al. | 514/54 |
| 6,057,135 A * | 5/2000 | Ibrahim et al. | 435/105 |
| 6,306,639 B1 | 10/2001 | Woods et al. | 435/252.3 |
| 6,333,181 B1 | 12/2001 | Ingram et al. | 435/165 |
| 6,423,145 B1 | 7/2002 | Nguyen et al. | 127/37 |
| 6,569,653 B1 | 5/2003 | Alard et al. | 435/161 |
| 6,660,506 B2 | 12/2003 | Nguyen et al. | 435/165 |
| 6,699,696 B2 | 3/2004 | Woods et al. | 435/161 |
| 6,927,048 B2 | 8/2005 | Verser et al. | 435/161 |
| 7,309,602 B2 * | 12/2007 | David | 435/254.2 |
| 2002/0137154 A1 * | 9/2002 | Ingram et al. | 435/161 |
| 2007/0031918 A1 * | 2/2007 | Dunson et al. | 435/41 |

FOREIGN PATENT DOCUMENTS

WO 88/09379 12/1988

* cited by examiner

*Primary Examiner*—Herbert J. Lilling
(74) *Attorney, Agent, or Firm*—Vidas, Arrett & Steinkraus, P.A.

(57) ABSTRACT

A method for producing ethanol from cellulose, the method including the steps of hydrolyzing said cellulose with enzymes produced by ethanologenic microorganisms to form a fermentable sugar or mixture of fermentable sugars, and fermenting the fermentable sugars with a yeast consortium to produce ethanol.

22 Claims, 4 Drawing Sheets

US 7,527,941 B1

PROCESS FOR PRODUCING ETHYL ALCOHOL FROM CELLULOSIC MATERIALS

FIELD OF THE INVENTION

The present invention relates generally to the production of ethyl alcohol by yeast fermentation of fermentable sugars produced as a result of saccharifying cellulosic materials.

BACKGROUND OF THE INVENTION

With the ever increasing world wide consumption of fossil fuels, there has been an ever increasing interest in alternative energy options. Considerable interest has now been focused on the use of ethanol.

Ethanol has been found to have widespread application in beverages and food, as an industrial chemical, as a gasoline additive, and now, even more importantly, as a fuel or gasoline replacement. Ethanol produces less toxic air emissions such as carbon monoxide, CO, than the hydrocarbon fossil fuels currently used. Furthermore, ethanol has the advantage of being a renewable resource, as opposed to fossil fuel oil which is finite. Use of ethanol can also reduce the nation's dependence on these finite and largely foreign fossil fuel sources. However, efficiently producing ethanol in sufficient quantities remains a concern.

Various sources and methods of ethanol production have been attempted to date. There has been an increasing interest in the use of cellulose waste or by-products as a source of ethanol production because these materials are often simply disposed of. Examples of such materials include the waste or by-products produced as a result of harvesting agricultural crops such as the stalks, hulls or husks from legumes, or waste from cows or bovines. After harvesting, for example, the unwanted hulls and husks of legumes may be used as animal feed or field spread for easy disposal. Animal wastes may also be field spread for easy disposal. It has become desirable to employ such cellulose by product materials for conversion to ethanol, particularly in light of the rising cost of fossil fuels.

Cellulose is a polymer of D-glucose molecules linked together via $\beta$-1,4 linkages. Prior to fermentation, these polymers are cleaved or depolymerized to form simple sugars. This process is sometimes referred to in the art as saccharification.

Cellulose, however, is very resistant to cleavage. Thus, it can be challenging to accomplish the conversion in an efficient, economic manner so as to produce sufficient quantities of sugars which can then be fermented to ethanol. However, once cellulose is converted to fermentable sugars such as glucose, the resulting sugar is easily fermented to ethanol using yeast. Thus, the difficult challenge of the process is to convert the cellulose to yeast fermentable sugars such as glucose.

Commonly employed methods of saccharification include acidic and enzymatic hydrolysis, and mechanical degradation, the latter typically being employed in combination with one of the other methods.

Acid hydrolysis involves the use of either concentrated or diluted mineral acids. In concentrated form, the acids can produce high yields of fermentable sugars such as glucose, are expensive and cause difficulties for disposal of the waste acid material. To improve the overall yield of acid hydrolysis using diluted acids, pretreatment of the cellulose has been employed, and/or enzymatic hydrolysis. Pretreatment involves mechanically and/or chemically treating the cellulose in order to break down the integrity of the fiber structure of the cellulose in order to make it more susceptible to attack by cellulose enzymes.

Mechanical treatment may involve pressure, grinding, milling agitation, shredding, compression/expansion, etc. Sonification or ultrasound are commonly employed in pretreatment of cellulose. Chemical methods involve the use of steam, acids or solvents. Many such pretreatment processes may leave a muddy pulp and undissolved solids.

Adding enzymes, on the other hand, improves the efficiency of the process, but significantly increases the cost of production making it economically inefficient for large scale production operations.

A further complication is that yeast have a limited ability to ferment sugars other than glucose. Many methods of converting cellulose to glucose, such as acid hydrolysis, produce sugars, in addition to glucose, such as xylose in rather large quantities, which are not yeast fermentable which further decreases the efficiency of the process.

There is a continuing need for efficiently and economically converting cellulose to yeast fermentable sugars which can then be fermented to ethanol.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

SUMMARY OF THE INVENTION

The present invention relates to an improved process for efficiently and economically producing ethanol and 2-propanol, and acetone from cellulose by fermentation of sugars produced as a result of saccharification of the cellulose without using acid hydrolysis, without using additional enzymes, and without mechanical or other pretreatment.

More particularly, the present invention relates to a process of converting cellulose to fermentable sugars using an inoculum of ethanologenic microorganisms, without additional enzymes, and then fermenting the fermentable sugars to ethanol using a yeast consortium which includes yeast, other fungi or mixtures thereof.

According to the invention, cellulose is converted to fermentable sugars via enzymatic hydrolysis using enzymes which are produced by the ethanologenic microorganisms.

The consortium of ethanologenic microorganisms may include bacteria, fungi or mixtures thereof.

Suitably the microorganisms are those that use a carbon source as an electron donor and $Fe^{+3}$ as an electron acceptor.

One source of iron which may be employed herein is magnetite.

Examples of suitable microorganisms include, but are not limited to, *Enterobacter cloacae, Geobacter metalloreducens, Clostridium* species, *Pseudomonas* species or mixtures thereof.

In a preferred embodiment, at least *Enterobacter cloacae* is employed in the consortium.

The consortium of ethanologic microorganisms are capable of converting cellulose to cellobiose, glucose, maltose or mixtures thereof. The resultant fermentable sugars can then be yeast fermented to ethanol using a consortium of yeast, other fungi or mixtures thereof.

The invention is not limited by the yeast which may be employed herein and any suitable yeast finds utility herein.

A small amount of oxygen may be added to the mix in order to discourage the growth of Methyl bacter which would produce methane under strictly anaerobic conditions. Alternatively, if the production of methane is desired, oxygen can be excluded and the fermentable sugars can be anaerobically digested to produce methane. The exclusion of oxygen encourages the growth of Methyl bacter and can drive the pathway toward formation of methane. Methane can be employed for operation of any gas appliances that use natural gas, for instance, such as stoves, furnaces, and gas dryers.

The ethanologic microorganisms for saccharification and the yeast consortium for fermentation may be added step-wise, or may be added to the cellulose simultaneously.

Sources of cellulose include, but are not limited to, leafy plants, legumes, cane sugar, sugar beets, amylaceous grains and tubers such as corn, sorghum, wheat, potatoes, rice, mylo, and the like.

Cellulose by-products or waste material are particularly suitable for use herein such as those derived from agricultural harvesting or processing agricultural products such as hulls, husks, stalks, pulp, etc. as well as animal waste.

The present invention has been found to greatly improve the yield of ethanol which can be obtained from the fermentation of such products to ethanol or methane, for example.

These and other aspects, embodiments and advantages of the present invention will become immediately apparent to those of ordinary skill in the art upon review of the Detailed Description and Claims to follow.

DETAILED DESCRIPTIONS OF THE PREFERRED EMBODIMENTS

Figure 1:
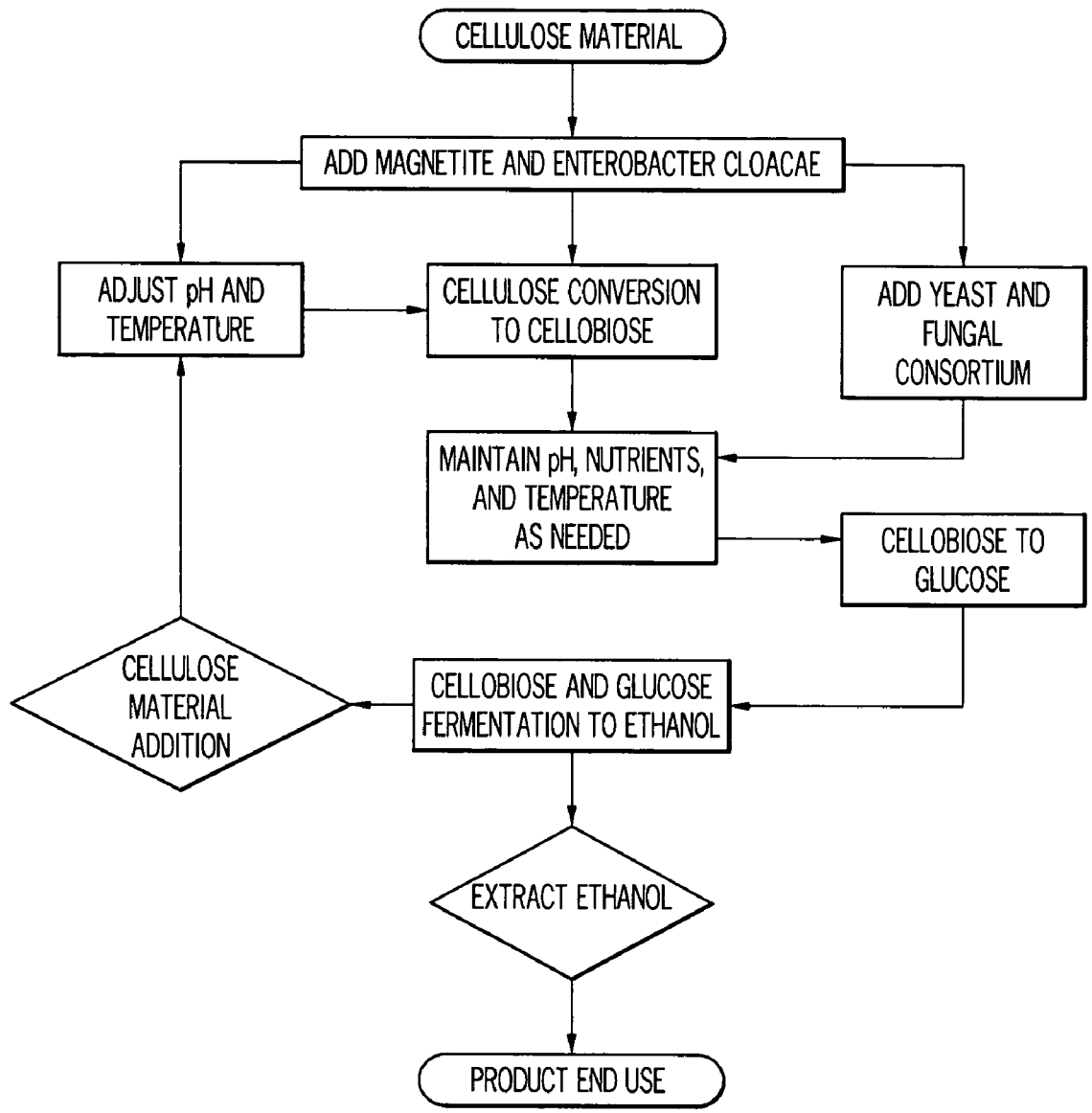
FIG. 1 is a block flow diagram illustrating the conversion of to ethanol in a specific embodiment which employs a bacterium to convert the cellulose to cellobiose, glucose and or maltose, and subsequent fermentation of these sugars with a yeast/fungal consortium.

While this invention may be embodied in many different forms, there are described in detail herein specific embodiments of the invention. This description is an exemplification of the principles of the invention and is not intended to limit the invention to the particular embodiments illustrated.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

This invention relates to the production of ethanol, particularly ethanol for use as a fuel, by saccharification of cellulose using ethanologic microorganisms to produce fermentable sugars, followed by fermentation of the fermentable sugars to produce ethanol and 2-propanol, and acetone.

In a broad sense, the method according to the invention includes a saccharification step in which a consortium of ethanologic microorganisms including at least one species of microorganism which uses carbon as an electron donor and $Fe^{+3}$ as an electron receptor, expresses enzymes which hydrolyze the cellulose to fermentable sugars. Fermentation can then be accomplished via a consortium of microorganisms including at least one species having the ability to ferment the fermentable sugars produced during the saccharification step, to ethanol. Alternatively, the process can be conducted anaerobically, and methane gas may be produced.

The term "consortium" as used herein, may refer to one or more species of microorganisms such as in a culture or inoculum.

Any suitable source of cellulose may be employed herein. Sources of cellulose include, but are not limited to, grain, tubers, vegetative sources, fruit, leafy plants, sugarcane and wood. More particularly, suitable sources include, but are not limited to, beets, corn, sorghum, wheat, potatoes, rice, mylo, and the like. Sources of cellulose for hydrolysis to fermentable sugars are discussed in U.S. Pat. Nos. 6,660,506 and 6,423,145, each of which is incorporated by reference herein in its entirety.

The present invention finds particular utility in converting cellulose by product material or cellulose waste to ethanol via enzymatic hydrolysis followed by yeast fermentation. The enzymes are produced by the ethanologic microorganisms. The cellulose is saccharified to the fermentable sugars, cellobiose, glucose, maltose or mixtures thereof.

By-products or waste from harvesting and processing of field crops are particularly advantageous for use in the process disclosed herein because such by-products or waste are typically disposed of. For example, hulls, husks, stalks, pulp from such products may be spread on a field for disposal or used as animal food usually low nutrition and cost. Cow and bovine manure are also commonly disposed of by spreading onto a field.

As used herein, the term "by product" shall refer to a variety of sources of cellulose including, but not limited to, hulls or husks from a variety of agricultural products such as legumes, stalks, leaves, animal waste, etc., which are often discarded and as such, find particular utility in the processes described herein. For example, suitable by product sources include, but are not limited to, sugar beet hulls and soy bean hulls, by product sugar beet pulp, spent corn mash, corn husks and corn stalks, etc.

Examples of animal waste which can be employed herein include the waste from cows or bovines. Cow manure has a cellulose content between about 50 wt-% to about 75 wt-%, more typically, cow manure is roughly ⅔ cellulose based on its total weight.

Figure 2:
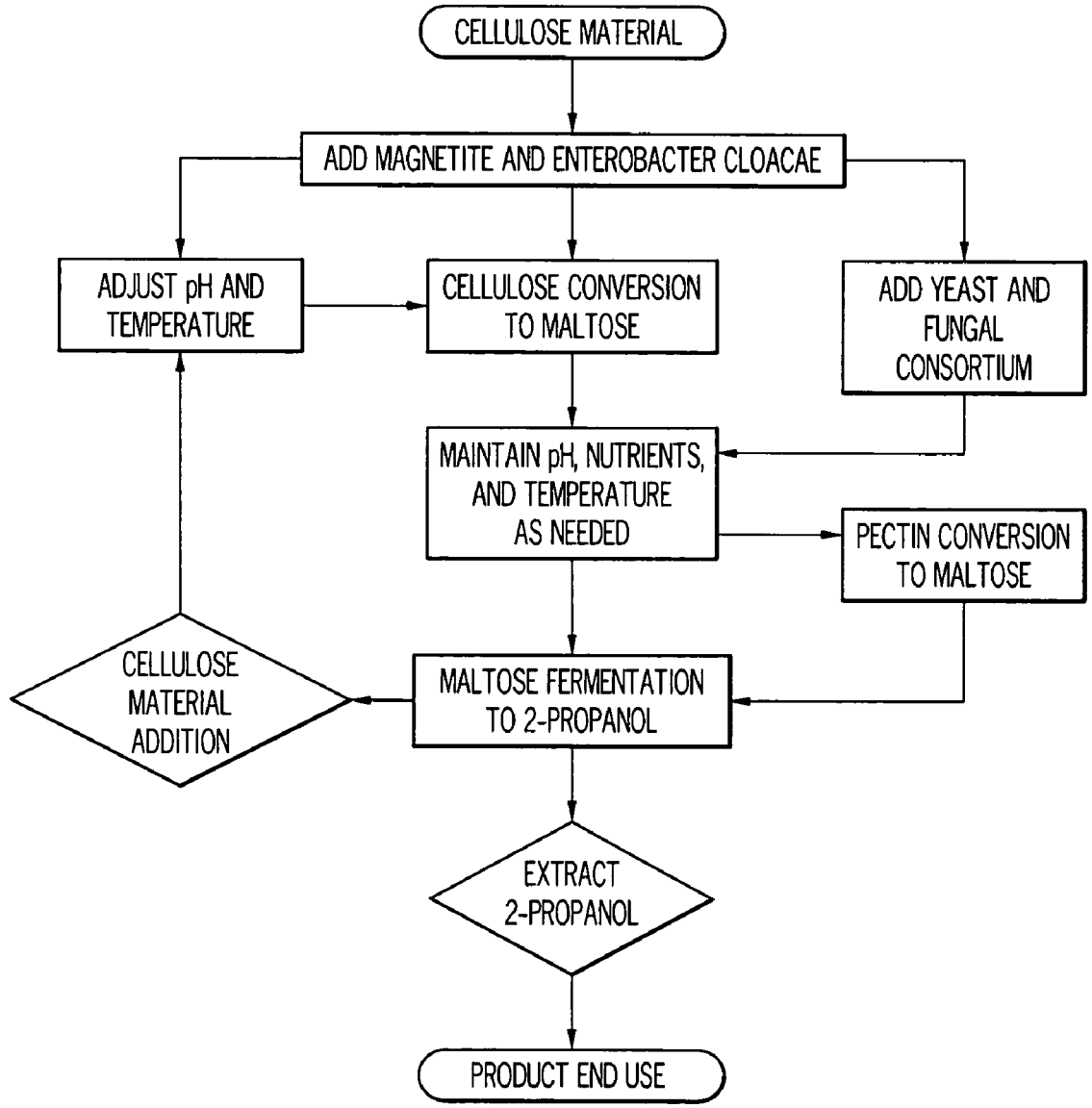
FIG. 2 is a block flow diagram similar to FIG. 1 wherein the same process is shown to produce 2-propanol.

Turning now to the figures, FIGS. 1-2 are block flow diagrams illustrating the process of converting cellulose derived from sugar beet pulp, a by-product obtained as a result of processing of sugar beets, to ethanol, 2-propanol or methane, according to the invention. Using sugar beet pulp is advantageous for ethanol production due to the enormous quantity of this pulp produced as a by-product of the sugar beet processing industry.

Referring to FIG. 1, in a first step, cellulose, derived from sugar beet pulp produced as a by-product of sugar beet harvesting and processing, is added to water in amounts between about 5% and 25% cellulose with the remainder being water. In this embodiment, a consortium of microorganism including *Enterobacter cloacae*, along with a source of $Fe^{+3}$, was added to the cellulose/water mixture. *Enterobacter cloacae* can be added in amounts of about 0.05% to about 1%, more typically about 0.1% to about 0.5% by volume. For example, 1000 ml of cellulose/water mixture can be inoculated with 1 ml of microbial consortium. These ranges are intended for illustrative purposes only, and not as a limitation on the scope of the present invention.

While the embodiment shown in FIGS. 1-2 employs a consortium including the species *Enterobacter cloacae*, other suitable microorganisms may also be employed and include, but are not limited to, members of the genus clostridium, members of the genus *Pseudomonas*, the species *Geobacter metalloreducens*, and the species *Shewanella putrefaciens*, for example, as well as mixtures thereof.

Suitably, the bacteria are mesophilic, thriving in mid-range temperatures of about 25° C. to about 35° C.

A source of iron may be added in amounts of about 0.05% to about 1%, and more typically about 0.1% to about 0.5% by weight to act as an electron acceptor for the *Enterobacter cloacae*. *Enterobacter cloacae* is an oxidative organism that operates well under anaerobic conditions, i.e. typically 85% to 95% substrate reduction is achieved only a small amount of oxygen may be added to shut down the Methyl bacter. Other suitable electron acceptors may also be employed and include, but are not limited to, nitrate ($NO_3$) and oxygen ($O_2$), as well as combinations of any suitable electron acceptors as well. The ranges are intended for illustrative purposes only, and not as a limitation on the scope of the present invention.

The electron donor is the beet pulp cellulose. The electron acceptor along with a micro-oxidative environment, encourage the β-1,4 linkages of the D-glucose units to break, i.e. via enzymatic hydrolysis, thereby producing cellobiose. The enzymes are produced by the ethanologenic microorganisms. No commercial enzymes are added.

The oxidation reduction potential of the reaction may range from about −65 millivolts to about −110 millivolts.

It is surmised that the cellobiose is further hydrolyzed to glucose and/or maltose. It is believed that the maltose is produced by partial hydrolysis of cellulose, or from the partial hydrolysis of pectin. Glucose is then fermented to ethanol while maltose is fermented to 2-propanol. Small amounts of acetone are also provided in the range of about 0.0% to 0.3% Consumable agricultural, i.e. plant, materials, may be composed of cellulose (a β-1,4-linked glucose polymer), hemicellulose (made up of polymers containing β-1,4-linked galactose and mannose), pectin (an α-1,4-linked polygalacturonic acid) and lignin (a polysaccharide phenolic polymer made up of a variety of phenylpropanes and guaiacyl, syringyl, p-hydroxyphenyl, and biphenyl nuclei.).

One suitable source of iron is magnetite (iron oxide, Fe3O4).

The microorganisms can be cultured using any suitable culturing medium as is known in the art. Brewer's thioglycollate medium is one example of a suitable culturing medium.

The contents are suitably mixed for 24 hours or as required. The pH is suitably between about 5 and 7 and more suitably between 5.5 and 6.5.

In the embodiment illustrated by FIG. 1, *Enterobacter cloacae* functions to produce enzymes for enzymatic hydrolysis of cellulose to cellobiose, a disaccharide (i.e. two glucose moieties in β-(1,4-linkage) which forms the basic repeating unit of cellulose and obtained by partial hydrolysis of the polysaccharide. *Enterobacter cloacae* has been found by the present inventors to very effectively and efficiently cleave cellulose bonds to produce cellobiose. The cellobiose is further hydrolyzed to glucose and/or maltose, maltose also a disaccharide, which can then be fermented using a yeast and/or fungal consortium to produce ethanol and 2-propanol. While glucose is primarily fermented to ethanol and a small amount of acetone, it is believed that maltose is primarily fermented to 2-propanol (FIG. 2).

Any yeast and/or other fungi suitable for fermentation of these simple sugars can be employed herein, and certain species of bacteria have also been found to be suitable for fermentation of the simple sugars. Examples of suitable yeast include, but are not limited to, species from the genus *Saccharomyces* such as *Saccharomyces cerevisiae* and *Saccharomyces pombe*, *Zymomonas mobilis*, and species from the genus *Brettanomyces* such as *Brettanomyces custersii* and *Brettanomyces bruxellensis*, etc. Examples of suitable yeast and/or other fungi can be found in U.S. Pat. Nos. 4,321,328 (*Sacchromyces Cerevisiae*), 5,100,791 (*Brettanomyces custersii*), 6,569,653, each of which is incorporated by reference herein in its entirety. These are intended for illustrative purposes only, and not as a limitation on the scope of the present invention. The invention is not limited by the type of yeast which may be employed providing the yeast can ferment cellobiose, glucose, maltose, or mixtures thereof.

Some bacteria can also ferment simple sugars. See, for example, U.S. Pat. Nos. 4,647,534, 4,731,329, 4,830,964, each of which is incorporated by reference herein in its entirety.

Preferable for use herein are those yeasts capable of fermenting glucose and/or maltose, or cellobiose if any is left, to ethanol. However, it would appear that the cellobiose is hydrolyzed to glucose and/or maltose during the saccharification step.

In the embodiment shown in FIGS. 1-2, a consortium including *Saccharomyces cerevisiae* has been found to be preferable for use in fermentation of the simple sugars produced as a result of saccharification of the cellulose beet pulp.

Fermentation may be suitably allowed to proceed for about 48 hours or as needed to either complete the fermentation process or to reach the desirable levels of ethanol production.

FIG. 1 illustrates a pathway for which ethanol is produced via saccharification of cellulose to cellobiose and glucose, and subsequent fermentation of glucose to ethanol. However, it has been found that 2-propanol and acetone may also be produced. With the addition of oxygen in amounts sufficient to discourage the growth of bacteria which produce methane, such as Methyl bacter, it has been found that ethanol is produced in amounts of about 10% to about 20%, 2-propanol in amounts of about 1% to about 10%, and acetone in amounts of about 0.1% to about 1%. Carbon dioxide is given off as a by-product. Oxygen may be added in small amounts of a few parts per billion to a few parts per trillion.

The process embodied in FIG. 1 has been found to produce 12.5% by weight ethanol (FIG. 1), 5% by weight of 2-propanol (FIG. 2), and 0.3% by weight of acetone with a 1 liter sample.

This is a substantially high yield of ethanol based on the initial amount of cellulose employed.

Alternatively, oxygen may be excluded from the process. In the event that oxygen is excluded, the growth of Methyl bacter may not be hindered, and methane may be produced. This process is shown as a blow flow diagram in FIG. 3. The process illustrated in FIG. 3 has been found to produce yields of methane as high as 80% by weight and 20% carbon dioxide. The range may be anywhere from about 40% to about 80% by weight methane yield.

Figure 3:
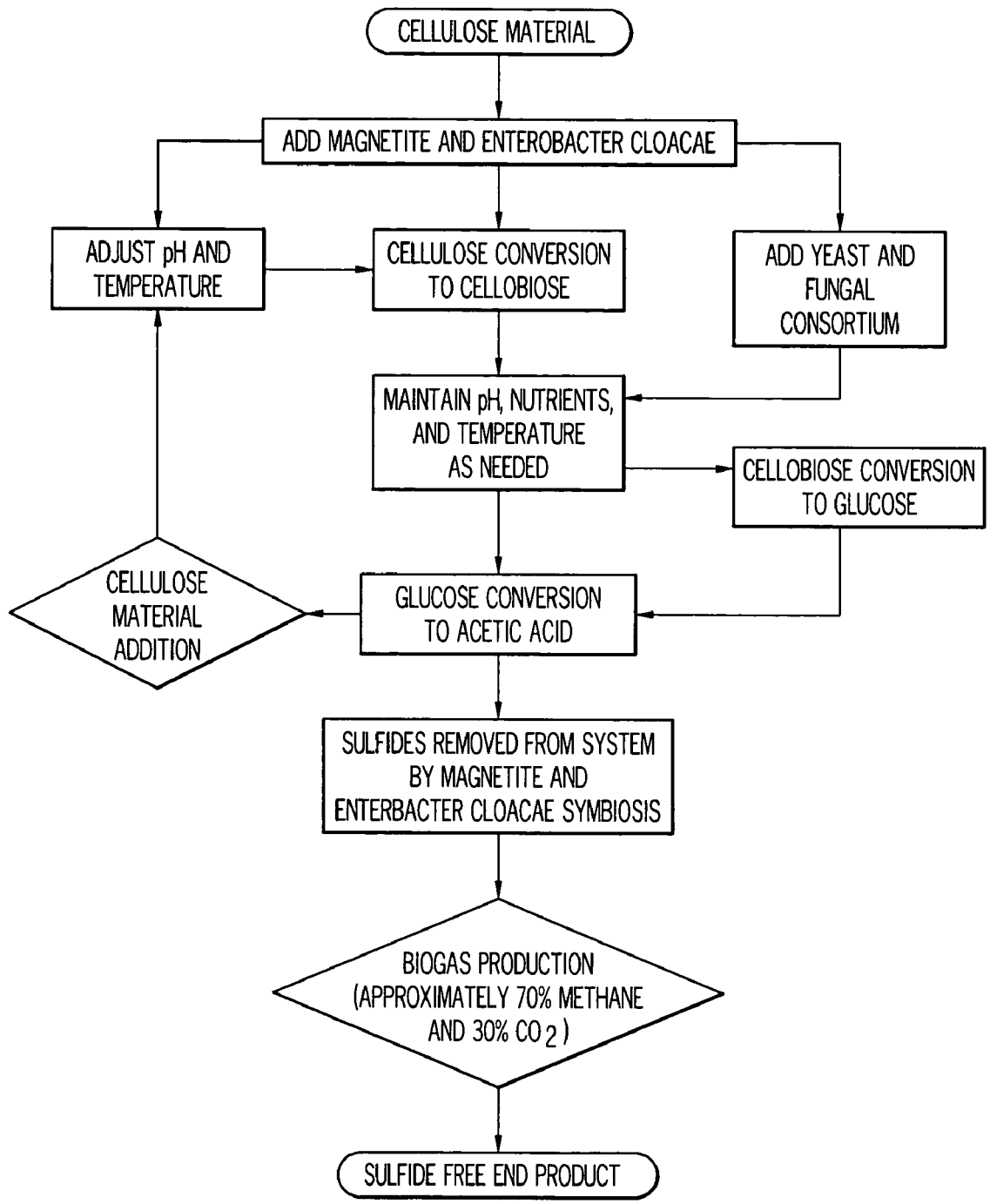
FIG. 3 is a block flow diagram similar to FIGS. 1 and 2 wherein the same process is shown to produce methane.

In FIGS. 1-3, the cellulose source is sugar beet pulp. Some sources of cellulose, such as sugar beet pulp, appear to be more readily hydrolyzed by these enzymes than other sources. For cellulose from sources which are more difficult to hydrolyze, a solvent may first be employed to begin cleavage of the cellulose. Suitable solvents include, for example, α-hydroxy acids or salts thereof, transition metal halides or oxides, and mixtures thereof.

For example, in one embodiment, a mixture of citric acid or sodium salt thereof, and ferric chloride ($FeCl_3$), is employed to begin hydrolysis of the cellulose. After addition of the solvent, the mixture may be heated to further induce hydrolysis of the cellulose.

The present invention can be adapted to either batch processing, or to continuous processing, such as by a zone mixed, plugged flow digester.

After processing, centrifugation can be employed to separate the liquid from any remaining solids, followed by distillation to obtain ethanol.

In one embodiment, double distillation, followed by treatment with a molecular sieve to take off any remaining water, was employed to obtain a pure ethanol product. 2-propanol and some acetone may also be obtained with this procedure. Molecular sieves can be advantageously regenerated and recycled using alternating tanks.

The present invention offers several advantages over currently employed methods of producing ethanol. One advantage is that the process does not require acid hydrolysis. Therefore, there is no problem with disposal of waste acid.

Further, the process according to the invention does not require the addition of any commercially generated enzymes. The enzymes employed are produced by the ethanologenic microorganisms. As commercially generated enzymes are expensive, the process according to the invention is more economical than those methods which do require additional commercial enzymes.

Yet another advantage in employing the method according to the invention is that saccharification and fermentation can be conducted in a single fermentation reactor if so desired. In a typical process, cellulose is treated with commercially extracted enzymes wherein optimum reactivity for saccharification is conducted under conditions of pH, oxidation potential and/or temperature, which is not conducive to yeast propagation. Therefore, the fermentation is typically conducted in another reactor.

A further advantage is the ability to be able to switch between producing ethanol or methane by the simple process of adding a small amount of oxygen for ethanol production and by excluding oxygen for methane production.

The process according to the invention also advantageously employs by-products from harvesting agricultural products which are very abundant.

The current invention is further illustrated by the following non-limiting examples.

EXAMPLE 1

Example 1 illustrates a process whereby a microbial and fungal consortium was employed to produce high grade ethanol and 2-propanol from by product sugar beet pulp.

The microbial inoculum was first prepared by adding approximately 1 ml of a stock solution including *Enterobacter cloacae* to 25 g of Brewer's thioglycollate medium and autoclaving at 120° C. for about 45 minutes. The medium is then cooled to about 30° C. Mass doubling time for the bacteria is approximately 15-20 minutes. After 24 hours, the bacterial population in the culture is approximately $1\times10^8$ to about $1\times10^9$.

Sugar beet pulp was mixed with water at a ratio of 25% sugar beet pulp to 75% water to produce an aqueous sugar beet pulp mixture. Sucrose and other constituents were harvested from the aqueous sugar beet pulp mixture leaving cellulose, hemi cellulose, and pectin.

A 1 liter sample was spiked at initiation with 0.2 to 0.3 milliliters of molasses per liter and glucose in an amount of 0.8 gram per liter of the aqueous sugar beet pulp mixture. From this point on, the ethanol generation process ran by itself without glucose supplement. Molasses was added only at startup.

The sugar beet pulp falls apart at the end of the hydrolysis.

As determined by High Performance Liquid Chromatography (HPLC), ethanol was obtained in an amount of about 3 grams of ethanol per liter of the aqueous sugar beet pulp mixture, or about 12.5% based on the total weight of ingredients put into the system.

A small amount of oxygen, from parts per billion to parts per trillion, was added to the process to inhibit the growth of methanogens such as Methyl bacter. Methanogens produce methane gas at the expense of ethanol production. Thus, exclusion of all oxygen can drive the system to methane gas production.

If so desired, methane gas can be generated by preventing oxygen inclusion in the reactor.

Table 1 illustrates the various components produced and the amount of each one produced over a 10 day period.

TABLE 1

| | PERCENT BY WEIGHT | | | | | |
|---|---|---|---|---|---|---|
| Day | dp3 | MALT-OSE | d-GLU-COSE | GYCEROL | ETH-ANOL | 2-PROPANOL |
| 1 | 0.02 | 0.01 | 0.00 | 0.00 | 0.00 | 0.00 |
| 2 | 0.64 | 0.01 | 0.02 | 0.00 | 0.33 | 0.00 |
| 3 | 0.08 | 0.00 | 0.00 | 0.08 | 0.38 | 0.01 |
| 4 | 0.00 | 1.02 | 0.00 | 0.00 | 0.32 | 0.19 |
| 5 | 0.91 | 0.00 | 0.00 | 0.02 | 1.10 | 0.01 |
| 6 | 0.00 | 1.27 | 0.00 | 0.00 | 0.99 | 0.21 |
| 7 | 0.00 | 1.45 | 0.00 | 0.00 | 0.75 | 0.26 |
| 8 | 0.00 | 1.55 | 0.00 | 0.00 | 1.29 | 0.37 |
| 9 | 0.00 | 1.35 | 0.00 | 0.00 | 2.09 | 0.48 |
| 10 | 0.00 | 1.38 | 0.00 | 0.00 | 2.10 | 0.47 |

Figure 4:
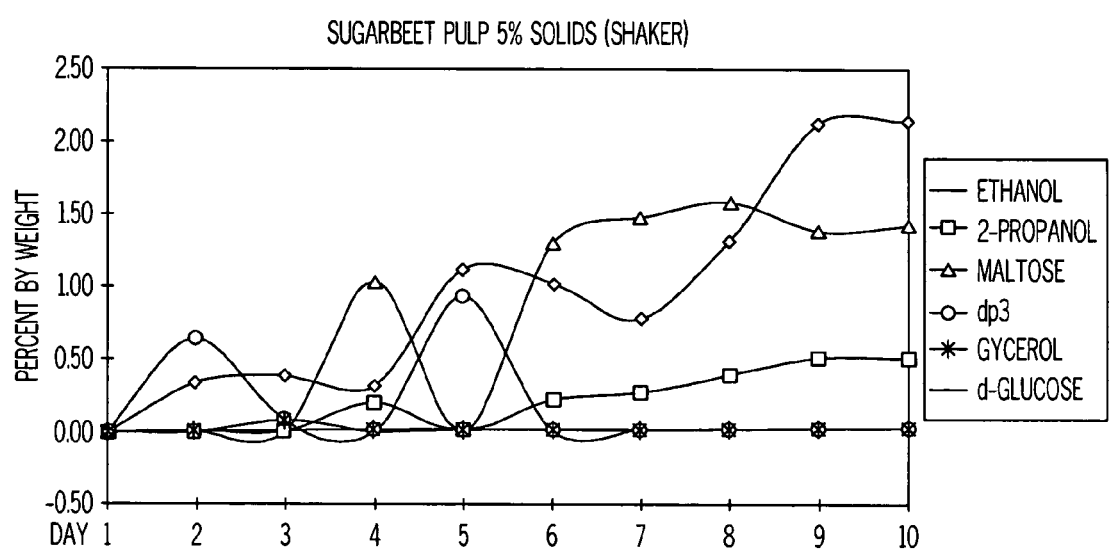
FIG. 4 is a graph illustrating conversion of sugar beet pulp to maltose, subsequently to d-glucose and ultimate fermentation to ethanol.

FIG. 4 is a graph showing the results of Example 1. The process exhibited about 85% efficiency providing an ethanol yield of 43%, and a 2-propanol yield of 9.6% by weight based on the total ingredient yield. The combined yield of alcohol is 52.4% by weight, or 67% by volume.

The graph illustrates a 10 day run of ethanol production. HPLC was performed on the reaction mixture each day.

The first cycle of the DP3 peak (3 carbon sugars) presented after 2 days. It is from this source that ethanol was generated. Substantially all of the 3 carbon sugars were consumed as carbon source.

The first cycle of maltose production appeared on day 4. The further hydrolysis of maltose generates two glucose molecules. The glucose was consumed so fast that it was not detectable after day 2.

The first ethanol peak appeared on day 2 and the first 2-propanol peak appeared on day 3.

A second peak representing the 3-carbon sugars appeared on the fifth day. A sharp increase in ethanol production accompanied the production of 3-carbon sugars.

From the sixth day on, the ethanol generated relied on the elevated hydrolysis of maltose.

EXAMPLE 2

It has been found that the maximum amount of ethanol which can be produced is limited by the yeast fermentation. Above about 12.5% ethanol, by weight of the total reactor ingredients, the yeast is poisoned by its own ethanol discharge and 2-propanol production begins.

Therefore, the amount of cellulose placed into the system was decreased for example 2.

The bacteria were cultured as described for Example 1, above. The following ingredients were employed:

900 g distilled water 100 g cellulose (sugar beet pulp)
Phosphorous and nitrogen were added 20 g yeast extract 1 g magnetite 10 g molasses 8 g dextrose 25 g Brewer's thioglycollate medium with bacteria 10 g Bacto-peptone protein source The following steps were followed:

1. The Brewer's thioglycollate medium was autoclaved at 120° C. for 45 minutes.

2. The medium was allowed to cool to 30° C.

3. The reactor, having the remaining ingredients, was inoculated with the medium having the bacteriological consortium at a pH between about 5.5 and 6.5

4. The total mixture was incubated at 30° C. in a shaker bath with a cap held loosely on the vessel for 3 days.

5. For ethanol, 2-propanol and acetone production incubation was continued for another week.

If methane production is desired, a gas-lock can be added to the reaction vessel after step 4 to exclude oxygen, and the reaction allowed to proceed anaerobically.

HPLC was employed to analyze the product. The resultant product had 12.5% ethanol, 5% propanol and 0.3% acetone.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

The invention claimed is:

1. A method for producing ethanol from cellulose, the method comprising the steps of:
   a) inoculating an aqueous mixture comprising said cellulose with a first consortium of ethanologenic microorganisms comprising bacteria, fungi or mixtures thereof, and said first consortium comprising at least one bacteria species which uses a carbon source as its electron donor and an electron receptor which is $Fe^{+3}$, said bacteria species expresses enzymes which hydrolyze said cellulose to produce fermentable sugars; and
   b) inoculating said aqueous mixture with a second consortium of microorganisms comprising at least one species which is capable of fermenting said fermentable sugars produced from step a); wherein the fermentable sugars are produced without using acid hydrolysis and without using additional enzymes.

2. The method of claim 1 wherein said fermentable sugars are selected from the group consisting of cellobiose, glucose, maltose and mixtures thereof.

3. The method of claim 1 wherein said inoculating step a) and said inoculating step b) are substantially simultaneous.

4. The method of claim 1 wherein said at least one bacteria species is mesophilic.

5. The method of claim 1 wherein said inoculating step a) and said incubating step b) are conducted at temperatures of about 25° C. to about 35° C.

6. The method of claim 1 wherein said first consortium of microorganisms comprises at least one bacteria species which is a member selected from the genus *Clostridium*, the genus *Pseudomonas*, the species *Shewanella putrefaciens*, the species *Enterobacter cloacae*, the species *Geobacter metallireducens*, and mixtures thereof.

7. The method of claim 1 wherein said first consortium comprises the species *Enterobacter cloacae*.

8. The method of claim 1 wherein said second consortium of microorganisms comprises a fungus or mixture of fungi.

9. The method of claim 8 wherein said fungus is yeast.

10. The method of claim 9 wherein said second consortium comprises at least yeast one yeast selected from the genus *Saccharomyces*.

11. The method of claim 10 wherein said second consortium comprises at least one yeast which is *Saccharomyces cerevisiae*.

12. The method of claim 1 further comprising:
    c) recovering ethanol produced from step b).

13. The method of claim 11 wherein said recovering step comprises distillation and treating with a molecular sieve.

14. The method of claim 1 wherein said method is free from added enzymes.

15. The method of claim 1 wherein said source of $Fe^{+3}$ is magnetite.

16. The method of claim 1 further comprising adding a small amount of oxygen during step a), during step b) or during both step a) and step b).

17. The method of claim 1 wherein said steps a) and b) are conducted in a single reaction vessel.

18. A method for producing fermentable sugars, the method comprising the steps of:
    a) providing a cellulose;
    b) adding to said source of cellulose a first consortium of ethanologenic microorganisms, said consortium comprising at least one bacteria species which uses carbon as an electron donor and $Fe^{+3}$ as an electron acceptor wherein said microorganisms produce enzymes sufficient for enzymatic hydrolysis of said cellulose to fermentable sugars; wherein the fermentable sugars are produced without using acid hydrolysis and without using additional enzymes.

19. The method of claim 18 wherein said fermentable sugars are selected from the group consisting of cellobiose, glucose, maltose and mixtures thereof.

20. The method of claim 18 wherein said first consortium comprises at least one bacteria species which is a member selected from the genus *Clostridium*, the genus *Pseudomonas*, the species *Shewanella putrefaciens*, the species *Enterobacter cloacae*, the species *Geobacter metallireducens*, and mixtures thereof.

21. The method of claim 18 wherein said first consortium comprises at least one bacteria species which is *Enterobacter cloacae*.

22. A method for producing ethanol from cellulose, the method comprising the steps of:
 a) inoculating an aqueous mixture comprising said cellulose with a first consortium of ethanologenic microorganisms comprising bacteria, fungi or mixtures thereof, and said first consortium comprising at least one bacteria species which is *Enterobacter Cloacae*, which expresses enzymes which hydrolyze said cellulose to produce fermentable sugars;
 b) inoculating said aqueous mixture with a second consortium of microorganisms comprising at least one species which is capable of fermenting said fermentable sugars produced from step a).

* * * * *